(12) United States Patent
Kranz et al.

(10) Patent No.: US 7,474,405 B2
(45) Date of Patent: Jan. 6, 2009

(54) MINIATURE FOURIER TRANSFORM SPECTROPHOTOMETER

(75) Inventors: Michael Scott Kranz, Madison, AL (US); Larry Christopher Heaton, Huntsville, AL (US); Calvin Wayne Long, Tullahoma, TN (US)

(73) Assignee: Morgan Research Corporation, Huntsville, AL (US)

( * ) Notice: Subject to any disclaimer, the term of this patent is extended or adjusted under 35 U.S.C. 154(b) by 0 days.

(21) Appl. No.: 12/033,927

(22) Filed: Feb. 20, 2008

(65) Prior Publication Data
US 2008/0198388 A1    Aug. 21, 2008

Related U.S. Application Data

(62) Division of application No. 11/282,235, filed on Nov. 18, 2005, now Pat. No. 7,359,058.

(60) Provisional application No. 60/629,073, filed on Nov. 18, 2004.

(51) Int. Cl.
*G01B 9/02* (2006.01)
(52) U.S. Cl. ........................... 356/450; 356/452
(58) Field of Classification Search .......... 345/450–456
See application file for complete search history.

(56) References Cited

U.S. PATENT DOCUMENTS

| | | | | |
|---|---|---|---|---|
| 4,309,109 A | * | 1/1982 | Blodgett et al. | 356/506 |
| 4,523,846 A | * | 6/1985 | Breckinridge et al. | 356/456 |
| 5,247,595 A | * | 9/1993 | Foldi | 385/78 |
| 6,249,346 B1 | | 6/2001 | Chen et al. | |
| 6,943,889 B2 | * | 9/2005 | Modavis | 356/451 |
| 7,050,171 B1 | * | 5/2006 | Banerjee et al. | 356/450 |

OTHER PUBLICATIONS

Thomas J. Suleski, Robert D. Te Kolste, Fabrication Trends for Free-Space Microoptics, Journal of Lightwave Technology, Feb. 2005, pp. 633-646, vol. 23, No. 2, IEEE.

Hakan Urey, Karlton D. Powell, Microlens array-based exit pupil expander for full color display applications, Proc. SPIE, vol. 5456, in Photon Management, Apr. 2004, Strasbourg, France.

(Continued)

*Primary Examiner*—Hwa (Andrew) S. Lee
(74) *Attorney, Agent, or Firm*—Greenberg Traurig LLP

(57) ABSTRACT

The Miniature Fourier Transform Spectrophotometer provides the capability, in a miniaturized device, of determining the light absorption/transmission spectra of a collected sample of gas or liquid though Fourier Transform spectroscopy techniques. The device takes an optical input from an optical fiber, manipulates that light through miniature optical components, and launches it into a miniaturized Michelson interferometer with a scanning mirror that acquires the interferogram of the optical input. The interferogram can be processed to retrieve the spectrum of the input light. A novel multi-stepped micro-mirror operates as the optical path length modulator in the miniaturized interferometer. A unique monolithic beamsplitter/mirror combination provides for accurate alignment of the components and greatly simplifies product integration. The device is designed to cover various optical spectra of interest. During operation, the precision and accuracy of the microfabricated components in the device allow operation and resolution even at extremely low wavelengths. In addition, the miniaturized nature of the device allows it to be used in new and extremely space-constrained applications.

8 Claims, 11 Drawing Sheets

Side View

OTHER PUBLICATIONS

E. Hasman, N. Davidson, A.A. Friesem, Heterostructure multilevel binary optics, Optics Letters, vol. 16, No. 19, Oct. 1, 1991, pp. 1460-1462, Optical Society of America.

Keiji Fuse, Takayuki Hirai, Toshihiko Ushiro, Takeshi Okada, Kenichi Kurisu, Keiji Ebata, Design and performance of multilevel phase fan-out diffractive optical elements for laser materials processing, Journal of Laser Applications, pp. 246-254, vol. 15, No. 4, Nov. 2003, Laser Institute of America.

* cited by examiner

MINIATURE FOURIER TRANSFORM SPECTROPHOTOMETER

REFERENCE TO RELATED APPLICATIONS

This application is a divisional of U.S. patent application Ser. No. 11/282,235, filed on Nov. 18, 2005, now U.S. Pat. No. 7,359,058, which is hereby incorporated by reference in its entirety, and is related to, and claims priority from Provisional Patent Application U.S. Ser. No. 60/629,073, entitled "Miniature Fourier Transform Spectrophotometer", filed on Nov. 18, 2004, which is fully incorporated herein by reference in ite entirety.

GOVERNMENT LICENSE RIGHTS

This invention was made with Government support under contract number FA8650-04-C-1715, awarded by the United States Air Force. The Government has certain rights in the invention.

FIELD OF THE INVENTION

The present invention relates generally to the field of Fourier transform spectroscopy. More particularly, the present invention relates to a micro-optoelectromechanical ("MOEMS") Fourier transform spectrophotometer.

BACKGROUND OF THE INVENTION

Embedding miniature sensors in products, systems, storage and shipping containers, and other items allows the monitoring of those items to determine health, maintenance needs, lifetime, and other item characteristics. Information from miniature chemical sensors can tell a user whether or not the item has been exposed to toxic or corrosive chemical levels that can cause damage, or has leaks of chemicals within the system.

In addition, there are increasing threats from chemical/bio agents and toxic industrial chemicals in both traditional military activities and in civilian sectors involving general public populations. This has resulted in a need for the widespread availability of instrumentation for the rapid detection of a growing number of chemical/bio agents. Military needs include historical agents such as organophosphorus and explosive chemicals, chlorine diphosgene choking gas and mustard gas blister agents, blood agents such as arsine, cyanogens or hydrogen chloride, nerve agents such as soman, tabun, or sarin, mycotoxin agents such as aflatoxin, botulinus, ricin, saxitoxin, trichothecene, or toxin producing bacteria such as anthrax. Peacetime and civilian chemicalibio agent detection interests include street drugs, environmental pollutants, disease outbreaks and leaking chemicals associated with a wide variety of containment vessels such as mobile and stationary storage tanks. Detection devices suitable for chemical/biological detection have enormous potential for application to civilian and government sponsored research and development activities, exploration, and commercial industry.

The growing number of potential chemical/bio agents and toxic industrial chemical locations, and the increasing rate of sampling engagements, have led to requirements for real-time detection, i.e. sampling times on the order of 100 ms or less. In addition, real-time detection of chemical and biological agents is becoming increasingly critical in a number of applications where the accessibility of detection instrumentation, or the ability to deliver the detection instrumentation on small platforms, is limited by power, volume and weight constraints. Furthermore, in the unmanned platforms, hand-held detectors, and portable systems currently envisioned in future military operational scenarios, the power and size requirements placed on detection systems are becoming harder to fulfill. These challenges have led to the need for novel miniature chemicalibio analysis systems, including miniature optical spectrometers. New technologies in optical sources, micro-optical integration, micro-electromechanical ("MEMS"), MOEMS and optical detectors have allowed these new miniature optical sensors, as well as enabled the incorporation of more sophisticated optical techniques into ever smaller packages.

In particular, the precise placement, alignment, and control of miniature optical components on MOEMS structures allows the extension of Fourier transform spectroscopic techniques that are dominant in infrared ("IR") spectroscopic instrumentation designs into the visible/UV spectrum with the capability of real-time detection of chemical and biological agents from small-unmanned delivery and reconnaissance platforms.

Several optical techniques have demonstrated an ability to uniquely identify chemical/bio agents, including fluorescence, emission, and absorption optical spectroscopy. Historically, absorbing spectroscopic techniques have dominated spectroscopic instrumentation from the ultraviolet ("UV") to the IR regions because both emission and fluorescence spectroscopy require the use of intense light sources at specific wavelengths to excite the electrons in chemical molecules to higher energy states where they decay with characteristic frequencies. This typically requires the use of large inefficient frequency doubled or tunable dye lasers to reach UV wavelengths, and can often be plagued by high intensity phenomena such as Raleigh scattering.

Absorption spectroscopy, however, can be used to measure chemical molecules with electron energy state transitions that occur in UV (200 nm to 400 nm) and visible wavelengths (400 nm to 800 nm), and is typically accomplished using optically dispersing elements such as prisms, or more commonly, diffraction gratings. However, diffraction spectrometers require implement slow mechanical scanning of an optical beam across a detector, or the use of a large linear electronically scanned detector array. A diffraction grating based design is typical of the state of the art spectrometer size reductions typified by the hand-sized or personal computer add-in card sized spectrometers offered commercially by various vendors. Absorption spectroscopy at longer near-IR ("NIR") to IR wavelengths (1,000 nm to beyond 30,000 nm or 30 um) is typically used to detect optical absorption associated with lower energy level molecular vibration excitation levels. This field of spectroscopy has been dominated by Fourier transform spectroscopy for many years because of several advantages over diffraction based optical designs. Fourier transform spectroscopy has greater optical efficiency, increased speed since the complete optical spectrum is measured simultaneously with an interferometric technique, increased sensitivity by allowing multiple scans, and reduced maintenance because it requires no external calibration and is mechanically simple with only linearly moving parts.

Historically, however, even though Fourier transform techniques are often preferred, they have been difficult to apply to UV and visible miniature spectrometer designs because of the strict demands on the precision of optical component placement, component movement, and system control mandated by operating at the shorter wavelengths. Although there have been large-scale designs (designated UVFT) proposed by university researchers, none are currently commercially available or known to have been actually fabricated and tested. However, emerging MOEMS technologies using lithography and etching techniques typical in semiconductor chip manufacturing enable the assembly of micro-optical components on physical features with tolerances of only a few hundred nanometers ($10^{-7}$ meters). In addition, electromechanical actuators can be fabricated in MOEMS structures that are capable of controlling and measuring motion to the same degree of precision. These new technologies can enable the development of UVFT spectroscopy and its application to chem/bio detection in unmanned systems, hand-held detectors, and portable analytical instruments.

SUMMARY OF THE INVENTION

It is therefore an object of the present invention to provide a miniature Fourier transform spectrophotometer using the precision of micromachined optical and MEMS components to operate in low wavelengths.

The present invention achieves this object by providing a miniaturized Fourier transform spectrophotometer that can be operated in the previously unattainable lower wavelength regimes including ultraviolet and visible spectra. The device applies a broadband optical source covering the spectra of interest to a specimen in a sample chamber which is analyzed by a miniature interferometer. The interferometer includes an input source, a collimating lens, a beamsplitter, a stationary mirror, a detector, and an optical path length modulator. The interferometer is a Michelson-type interferometer that has been miniaturized into a monolithic device. The precision of alignment tolerances achievable in this MOEMS device enables the device to operate in lower wavelengths than previously attainable, namely from 200 to 800 nm.

For purposes of summarizing the invention, certain aspects, advantages, and novel features of the invention have been described herein. It is to be understood that not necessarily all such advantages may be achieved in accordance with any one particular embodiment of the invention. Thus, the invention may be embodied or carried out in a manner that achieves or optimizes one advantage or group of advantages as taught herein without necessarily achieving other advantages as may be taught or suggested herein.

These and other embodiments of the present invention will also become readily apparent to those skilled in the art from the following detailed description of the embodiments having reference to the attached figures, the invention not being limited to any particular embodiment(s) disclosed.

Figure 1:
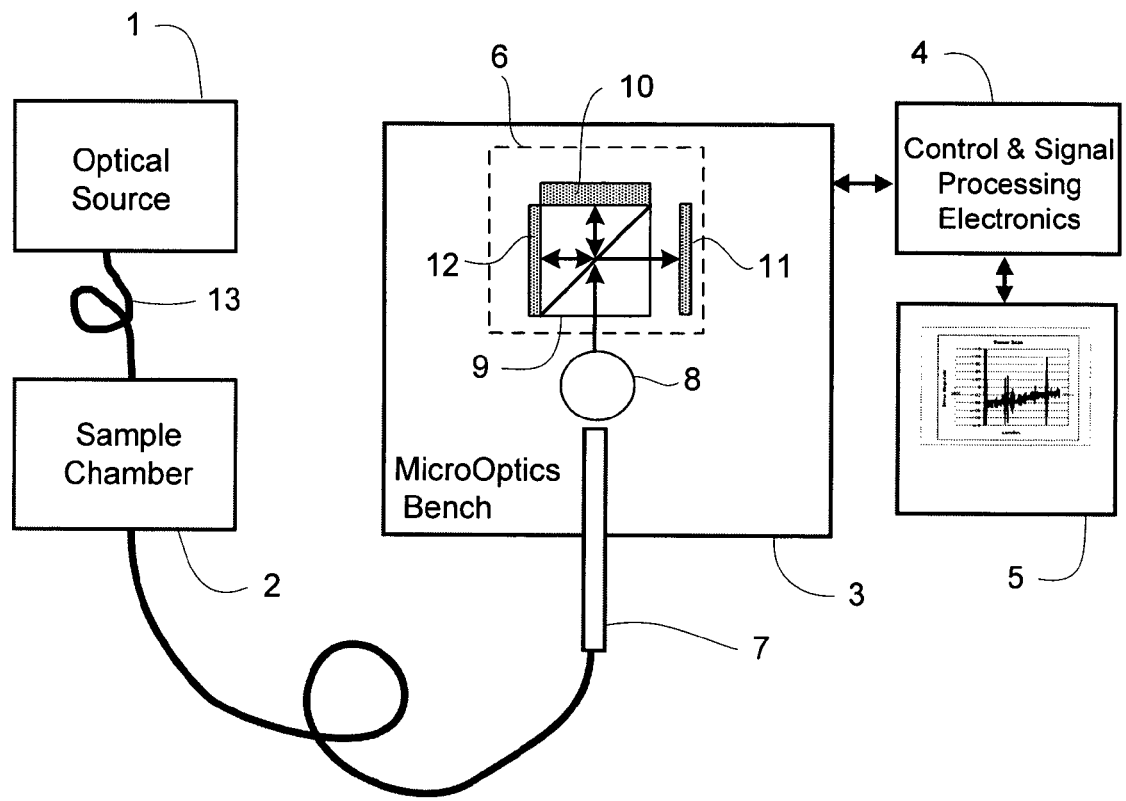
FIG. 1 is a block diagram of the miniature spectrophotometer and its components.

Repeat use of reference characters throughout the present specification and appended drawings is intended to represent the same or analogous features or elements of the invention

DETAILED DESCRIPTION

The present invention and its advantages are best understood by referring to the drawings. The elements of the drawings are not necessarily to scale, emphasis instead being placed upon clearly illustrating the principles of the invention.

FIG. 1 is a block diagram of the invention, which is comprised of an optical source 1, a sample chamber 2, a microoptics bench 3, signal processing electronics 4 and a graphical user interface 5. The microoptics bench 3 holds the fundamental component of the Fourier transform spectrophotometer: a miniature interferometer 6 able to operate at UV, visible, and NIR wavelengths. The interferometer 6 includes a cube beamsplitter 9, a stationary mirror 10, a detector 11, and an optical path length modulator (multimirror) 12.

When a sample is placed in a sample chamber 2, the optical source 1 is turned on and transmits light through an optical fiber 13 into the sample chamber 2. The light then exits the sample chamber 2 and enters the miniature interferometer 6 through an input source 7 (an optical fiber in some embodiments) and collimating lens 8.

Figure 2:
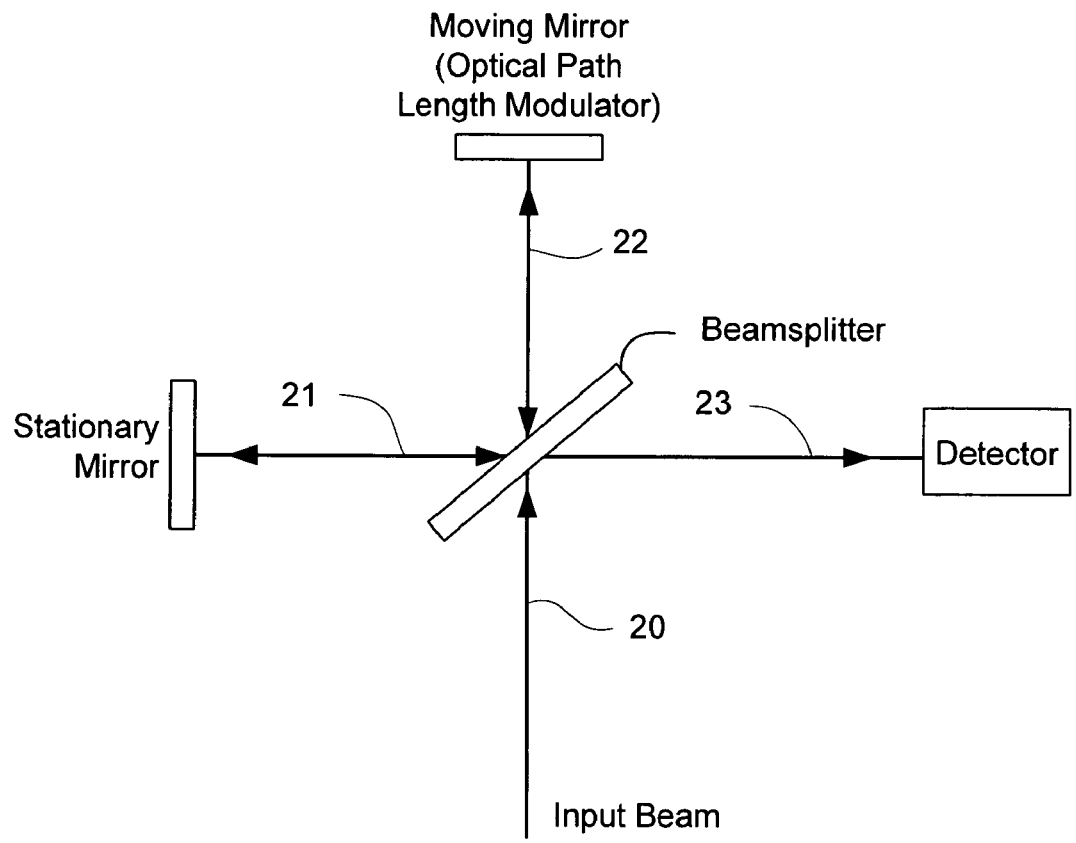
FIG. 2 is a diagram of a prior art standard Michelson interferometer.
Figure 3:
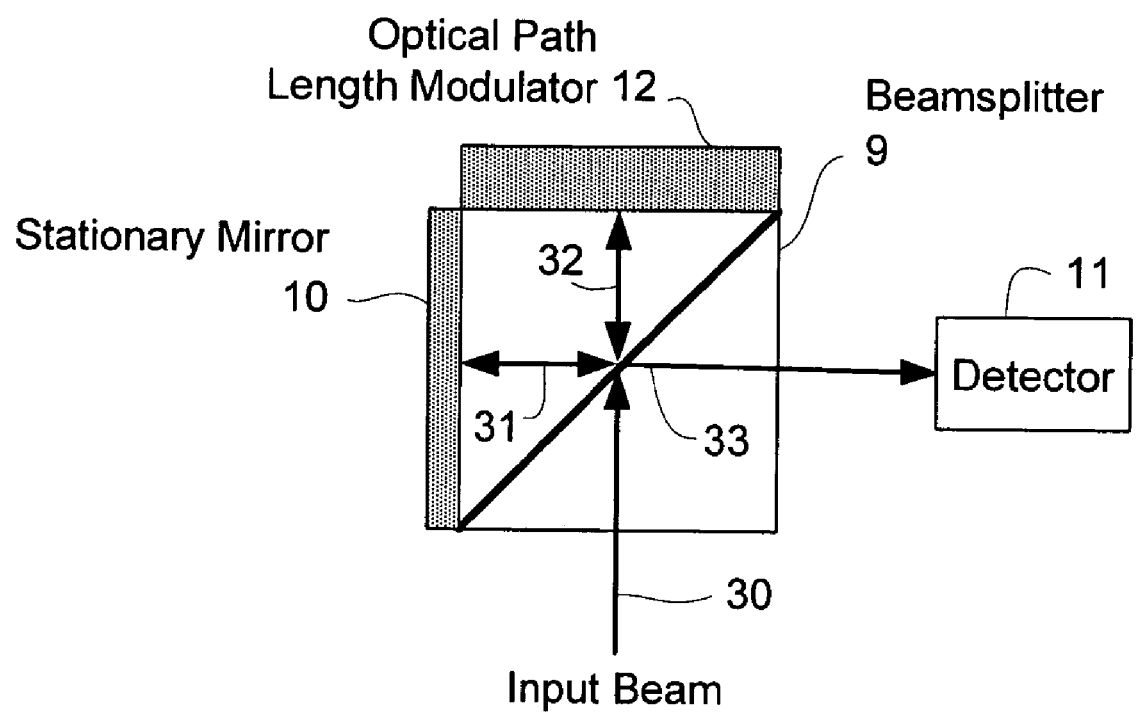
FIG. 3 is a diagram of the interferometer in the present invention.

A standard prior art Michelson Interferometer (illustrated in FIG. 2) contains four (4) beam paths or legs that are represented by an entrance path 20, static path 21, differential path 22, and detector path 23. As is shown in FIG. 3, the present invention contains all of the standard paths (entrance path 30, static path 31, differential path 32 and detector path 33), but, in the miniaturization of the interferometer, the distances between the interferometer components and the cube beamsplitter 9 have been shortened from those of the prior art. In fact, the stationary mirror 10 and the optical path length modulator (multimirror) 12 are adhered to the surface of the cube beamsplitter to make one monolithic device.

The optical path length modulator (multimirror) 12 alters the length of the differential path 32, thereby scanning the interferogram of the input light onto the detector 11. The output of the detector 11 is collected and filtered by the signal processing electronics 4, and a Fourier transform is performed on the resulting data. The spectrum returned from the transform can then be displayed on the graphical user interface 5 or stored in memory.

The precision and accuracy of the miniature optical components, as well as the use of microfabricated actuators and mirrors elements in the optical path length modulator allows the device to function at low wavelengths. At low wavelengths of light, very small imperfections and errors in tolerances can create large errors in the output. This invention utilizes microfabrication capabilities to minimize errors, thereby allowing operation in low optical wavelength regimes.

Figure 4:
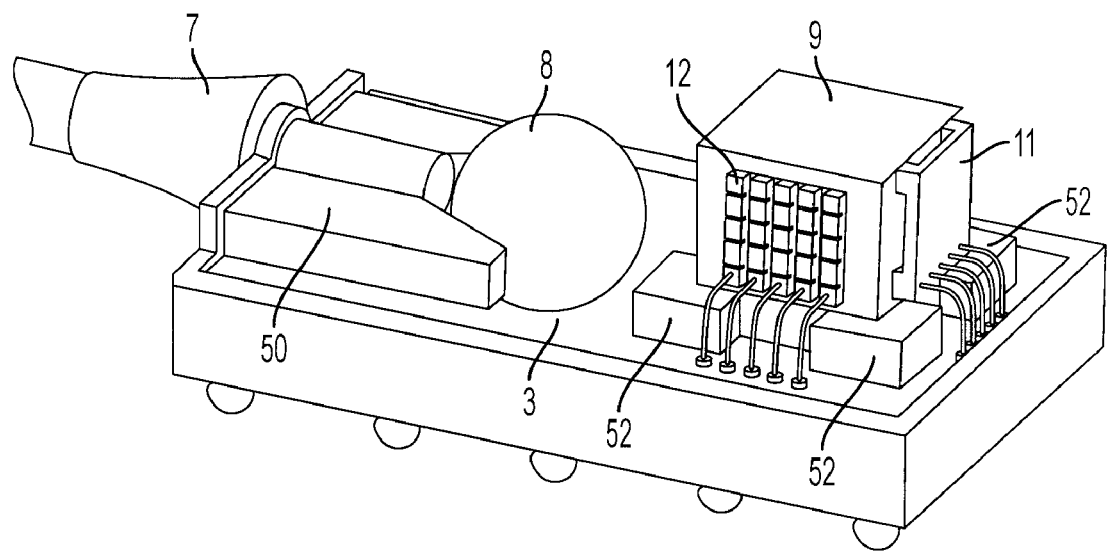
FIG. 4 is a three-dimensional view of one embodiment of the spectrophotometer.
Figure 5:
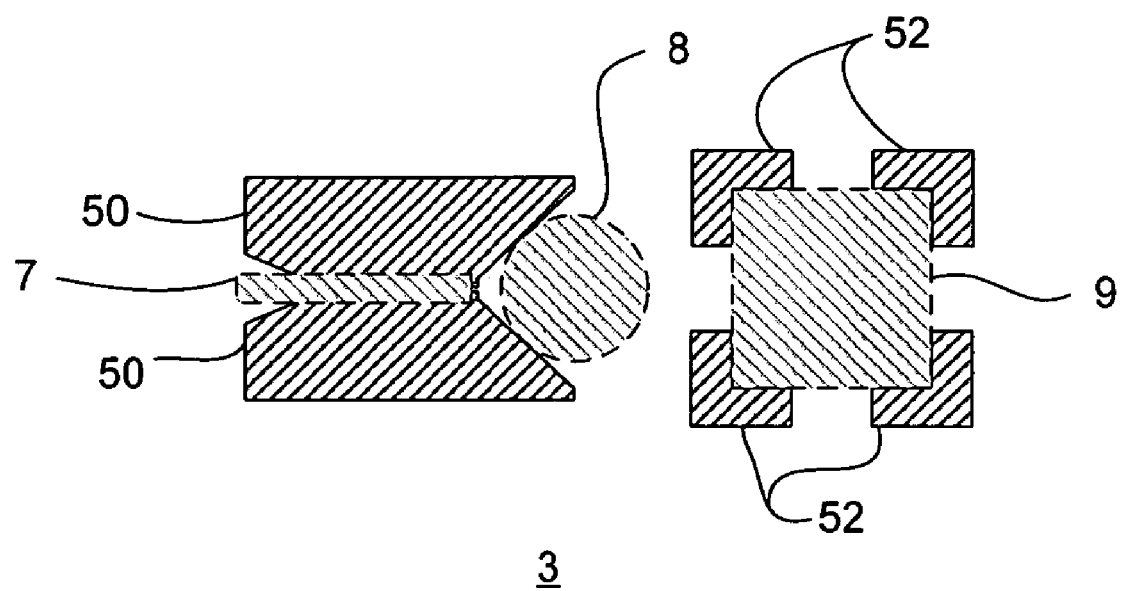
FIG. 5 illustrates the mounting positions of the interferometer components onto the microoptics bench.
Figure 6:
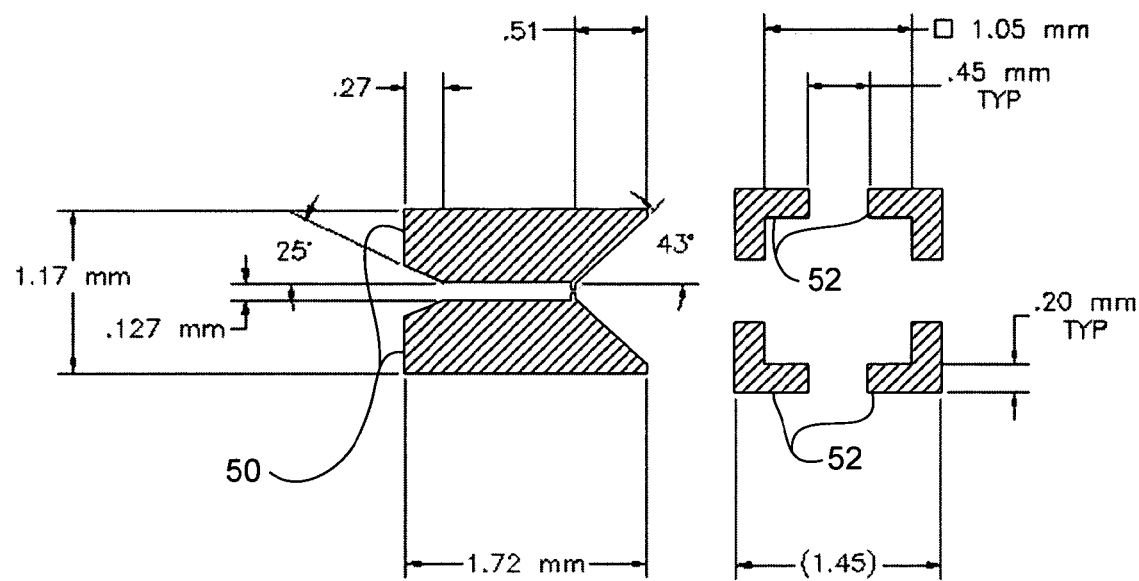
FIG. 6 shows the dimensions of one embodiment of the mountings on the microoptics bench.

The interferometer 6, one embodiment of which shown in three-dimensional form in FIG. 4, utilizes an input optical fiber 7, a ball lens collimator 8, and a cube beamsplitter 9 mounted to a microoptics bench 3. The microoptics bench 3 is fabricated in a thick layer of silicon or other micromachinable substrate onto which set of alignment features and jigs are etched using highly precise optical lithography to define the patterns. FIG. 5 shows one possible layout of micromachined mounting structures that have been used to realize precise placement of the optical components required for forming the miniature interferometer 6. As shown in FIG. 5, the microoptics bench 3 has mounting structures designed to hold the input optical fiber 7, ball lens collimator 8, and cube beamsplitter 9. FIG. 5 also illustrates possible positioning of the optical fiber/collimator mount 50 and the beamsplitter mount 52. In the embodiment illustrated in FIG. 5, the beamsplitter mount 52 consists of four (4) L-shaped mountings into which the cube beamsplitter 9 is fitted and adhered. The optical fiber/collimator mount 50 consists of mirror-imaged mountings that serve the dual purpose of holding the input optical fiber 7 and the collimator 8. The dimensions for the set of mountings used in one embodiment of the invention are shown in FIG. 6. Other configurations of mountings could also be used.

Figure 7:
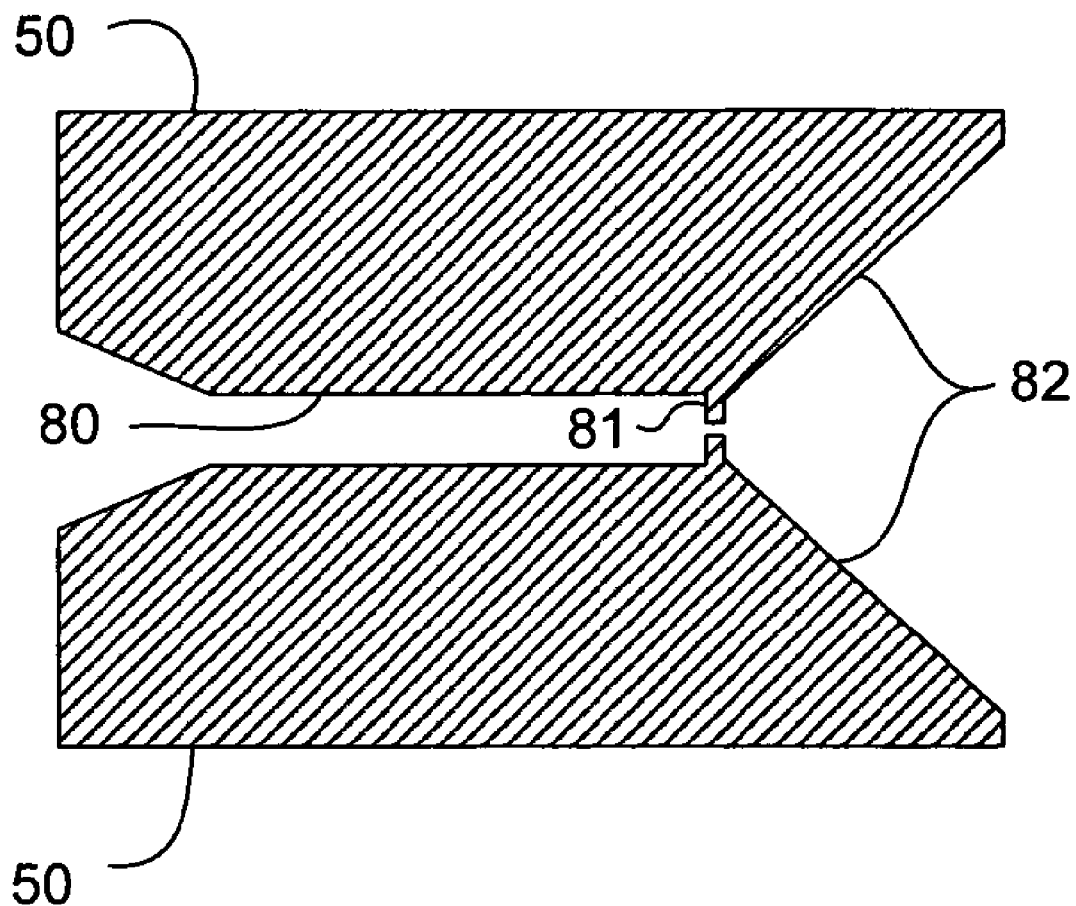
FIG. 7 shows one embodiment of the mount for the input fiber and collimator.

The mounting structure 50 for the optical fiber and ball lens combination contains alignment features that are important as its quality of alignment is critical to the ability to collimate the input optical light. There is typically sufficient variation in the ball lens diameter to make it difficult to position and align the lens to get high quality alignment, and that usually requires provisions for active alignment. However, the alignment structure on the microoptics bench 3 was specially designed to allow variation in the ball lens without altering the focal distances and collimation capability. As is shown in FIG. 7, the mounting structure 50 typically consists of a channel 80 into which an optical fiber (not illustrated) is placed and butted up against a small opening 81 at the end of the channel. This opening sets the output point from the optical fiber. For a ball lens, the focal length of the lens is a function of the diameter of the lens. For optical collimation, the distance from the ball lens to the output of the fiber needs to be equal to the diameter of the lens. The ball lens is inserted into its alignment structure and butted up against the walls 82 of the structure. The angle of those walls is set at the specific angle of 43 degrees. At this angle, even if a ball lens of a different diameter is used, the distance of the center of the lens from the output of the fiber also changes, and in exactly the correct amount to negate the impact of the focal length change. This allows collimation regardless of variations in ball lens size.

After fabrication of the microoptics bench 3, the microoptical components forming the interferometer are placed into their respective mounts and attached with a UV-curable adhesive. The mounts on the microoptics bench thus perform both alignment and attachment functions.

In addition, the beamsplitter 9 in the interferometer serves a number of purposes. First, it functions as the beam-splitting element required for interferometer operation. In addition, it is a mounting structure onto which the stationary mirror 10 and the optical path length modulator 11 can be attached. The beamsplitter 9 is fabricated from two prisms of fused silica that are bonded together. Materials other than fused silica could also be used, depending upon the wavelengths being investigated and the operational equipment used. A typical embodiment of the beamsplitter is 12.5 cubic millimeters, though other sizes could be used.

Figure 8:
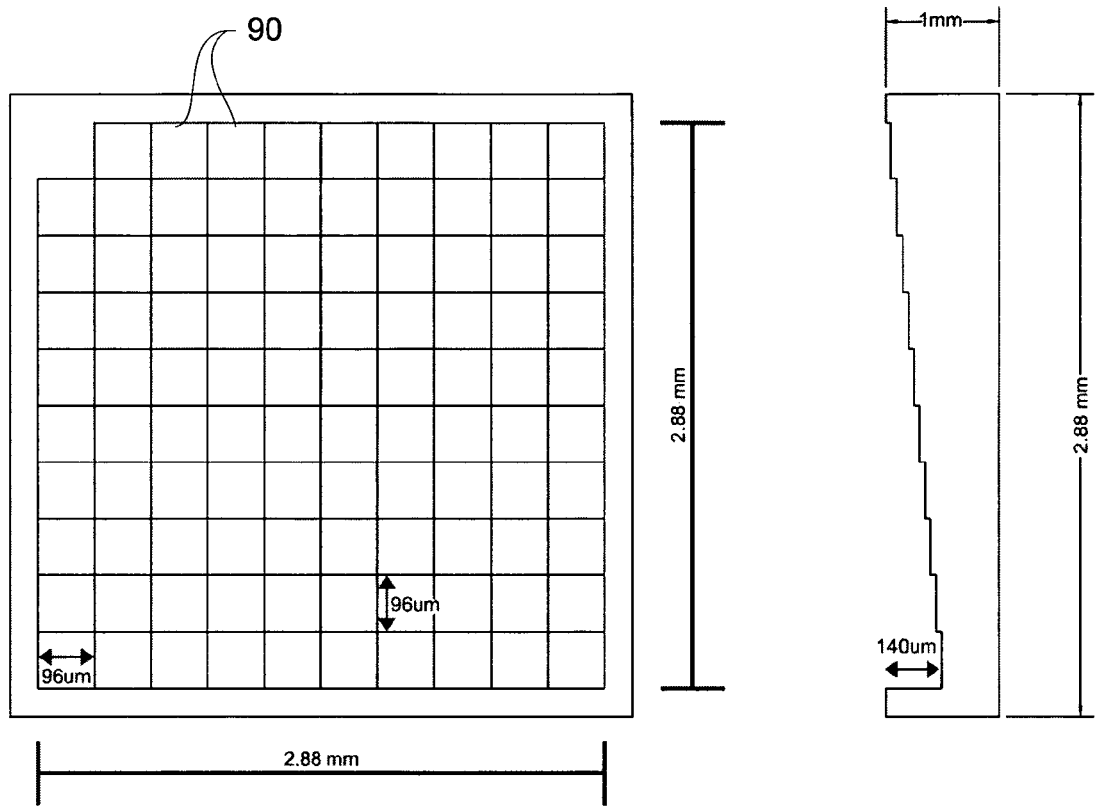
FIG. 8 shows the dimensions of one embodiment of the multimirror.

The optical path length modulator 12 is a critical component of the miniature spectrophotometer. In most conventional Michelson interferometers (illustrated in FIG. 2), the optical path length modulator alters the length of the differential path with a moving mirror. The challenges of miniaturizing the optical components into a rugged sensor make a moving mirror impractical. One embodiment of the present invention thus overcomes these difficulties by using a fixed stepped multimirror optical element as the optical path length modulator. FIG. 8 illustrates front and side views of the active area of the multimirror element. The multimirror consists of a large array of individual flat steps 90 etched into a substrate at differing depths. A fused silica substrate was used in one embodiment of the invention, though alternative materials could also be used, depending on the wavelengths being investigated and the operational equipment used to analyze the resulting data. Each flat step is etched at a different depth and then coated with a reflective material such as UV-enhanced aluminum. The resulting device represents a large array of stationary micromirror elements each separated by a specific distance corresponding to the positions that a scanning mirror would occupy in a traditional interferometer. This optical element can be bonded to the beamsplitter and assembled into the interferometer. Although FIG. 8 illustrates a 10-step by 10-step mirror array with one hundred (100) total steps, this number of steps is illustrated merely for the sake of clarity in illustrating the individual steps. In addition, the dimension of 140 micrometers in FIG. 8 is intended to represent the distance between the overall "highest" step and the overall "lowest" step, and not the difference within one column of steps. The preferred embodiment of the invention for analyzing the desired wavelengths contains a 30×30 array with 900 steps. In this embodiment, each step is 96 micrometers square, and the active area of the multimirror is approximately three square millimeters. Other sizes of mirror arrays with different numbers of steps could also be used, depending on the wavelengths of interest, required resolution, and detector used in the system.

Figure 9:
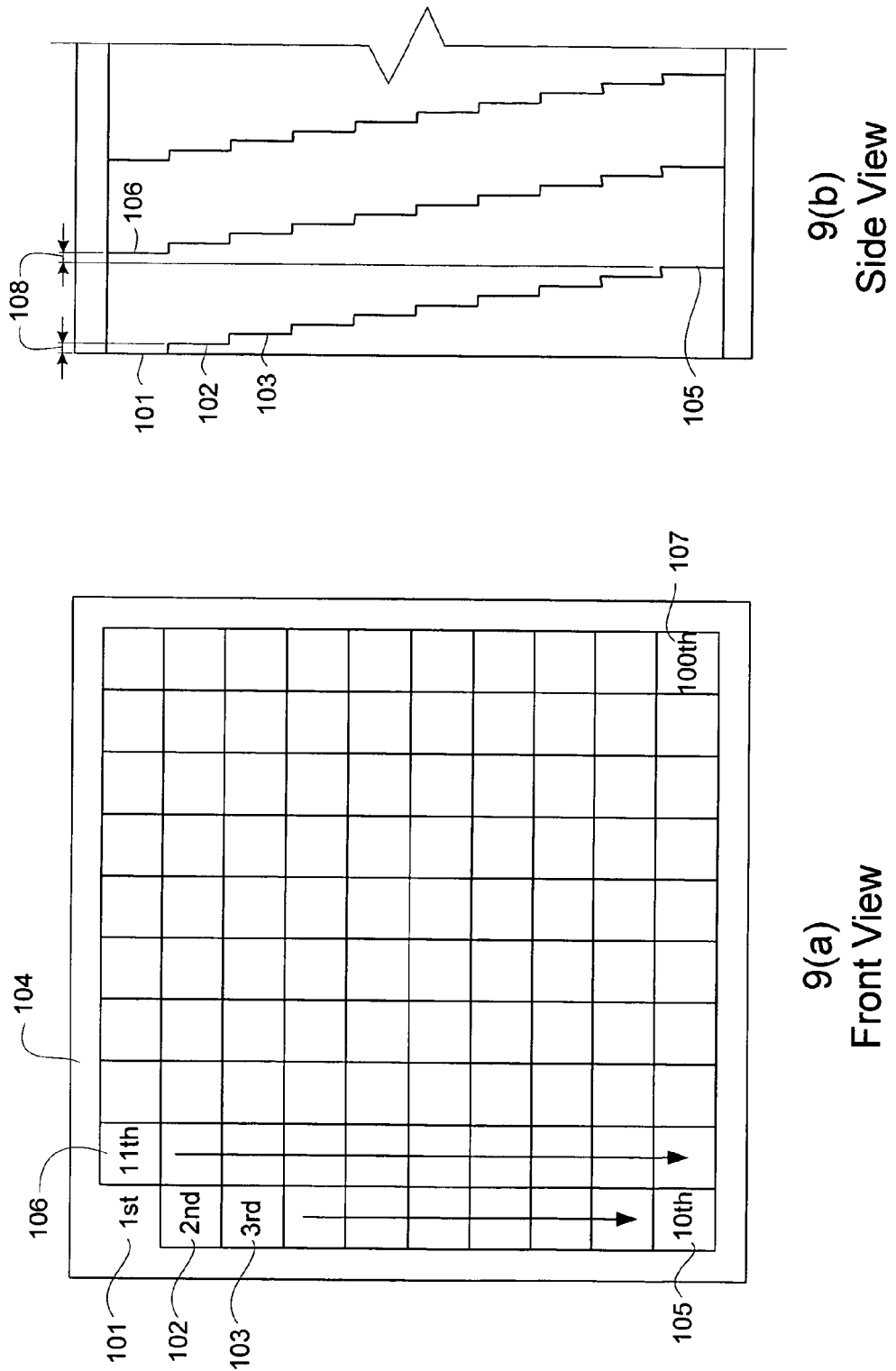
FIG. 9 illustrates the configuration of the steps in the multimirror.

FIG. 9 further illustrates the configuration of the stepped multimirror, again with one hundred (100) steps for illustrative purposes only. FIGS. 9(a) and FIG. 9(b), a front and side view of the multimirror respectively, shows that the "1st" step 101 is on the same level as the surface of the substrate 104. The "2nd" step 102 then "steps down" a distance equal to the step depth 108. Likewise, the "3rd" step 103 then steps down another step depth. This stepping down in equal increments continues to the "10th" step 105, which is the lowest step in the first column of the multimirror's steps. As is illustrated in FIG. 9(b), the "11th" step 106, the first step in the second column of steps, is one step depth deeper than the 10th step 105. The highest step in each successive column is thus lower than the lowest step in the previous column by a distance of one step length. This stepping process continues to the "100th" step 107, which is the deepest step.

Other embodiments of the invention may employ different stepping configurations, such as concentric "spirals" of quadrants of steps, without departing from the scope of the present invention.

Using the multimirror as the optical path length modulator requires the use of an array detector, in which a single pixel or a group of pixels in the array detector is aligned to one of the flat mirrors in the multimirror element. When operating, each pixel and mirror combination acts as a single small interferometer with a stationary optical path length difference. Taken as a whole, the entire interferometer is actually an array of much smaller interferometers, each with a specific path length difference and a dedicated detector. To retrieve the spectrum of the input, the device can simply acquire all of the data from the array detector in a parallel fashion, interleave it to form a standard one-dimensional interferogram, and perform conventional processing to obtain the spectrum from the interferogram. In the alternative, the control and signal processing electronics in the spectrometer could analyze the two-dimensional interference pattern, or interferomap, using look-up tables to compare the interference pattern to known images in order to identify the sample.

Figure 10A:
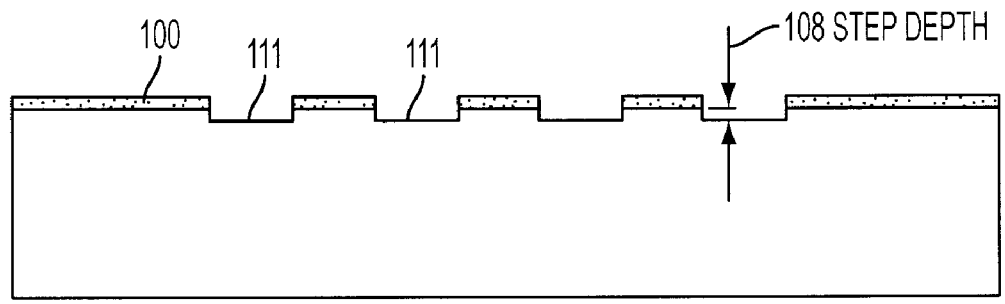
FIG. 10 shows the fabrication process for the steps in one embodiment of the multimirror.
Figure 10B:
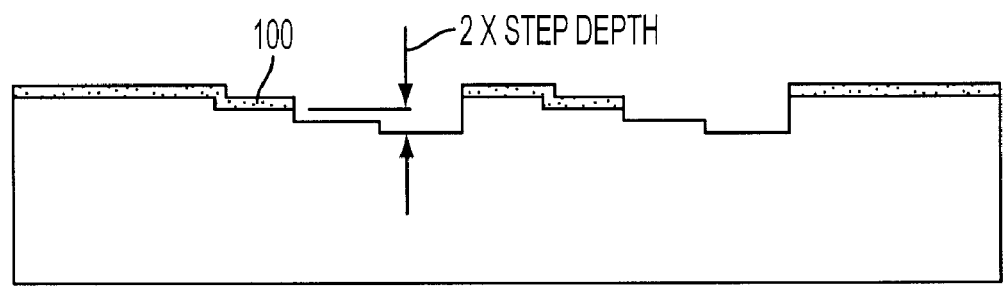
Figure 10C:
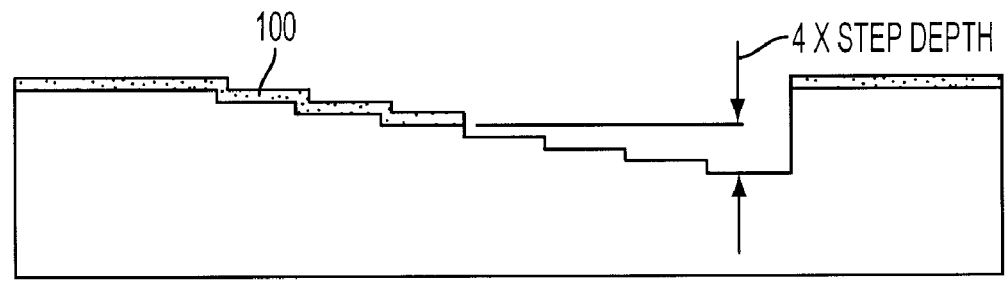

The multimirror optical element can be fabricated using a multilevel binary process that has been previously developed for fabrication of diffractive and refractive optical elements. A key feature of the process is that it allows the creation of $2^n$ etch levels where n is the number of etching steps. The masking steps illustrated in FIGS. 10(a)-10(c), show how an eight (8) level ($2^3$ level) device can be created from three (3) etching steps. First step levels 111 are created by application of photoresist 100 and etching to the step depth 108 as shown in FIG. 10(a). Next, lower step levels are created by masking as shown in FIG. 10(b) and etching to twice the step depth 108. The lowest step is at a depth of four times the step depth at this point. Then, by masking as shown in FIG. 10(c) and etching the material to four (4) times the step depth 108, the lowest step becomes eight (8) times the step depth, and a uniform set of eight (8) steps is created. This process can be repeated to create the 900 steps in the preferred embodiment, or any other configuration of $2^n$ levels.

The stationary mirror is a flat plate of fused silica coated with a reflective material such as UV-enhanced aluminum. Materials other than fused silica would also be used, depending upon the wavelengths being investigated and the operational equipment used. Both the stationary mirror and the multimirror are bonded to the cube beamsplitter using a water bonding method at the non-etched surfaces and the optically flat cube beamsplitter with a UV-curable epoxy along the edges to ensure a permanent bond.

Figure 11:
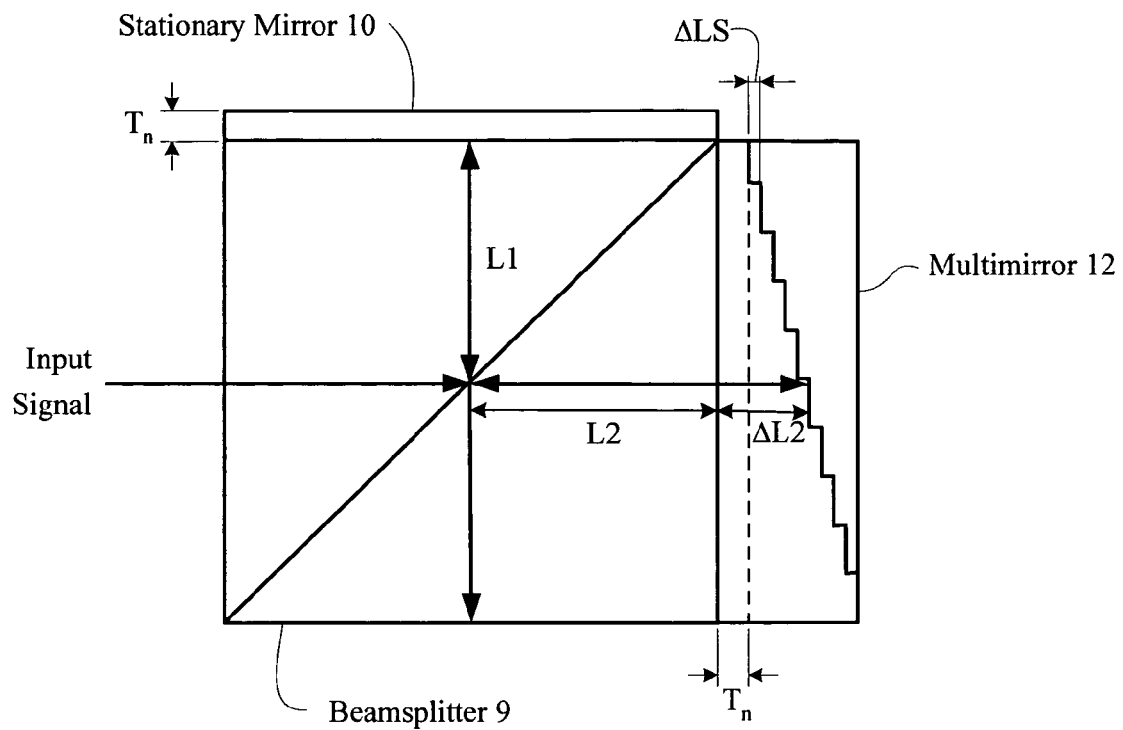
FIG. 11 shows the definition of parameters used in the design of the spectrophotometer.

FIG. 11 shows the definition of the primary parameters used to design the microspectrophotometer. As an initial matter, note that the first step of the multimirror 12 is offset from the beamsplitter 9 a distance of $T_n$, which needs to equal the thickness of the stationary mirror 10 to nullify the effect of the thickness of the stationary mirror 12. This offset is not an air gap, but is an added thickness of the multimirror's substrate material.

In the miniature interferometer, the nominal lengths of each leg are given by L1 and L2. There are N mirrors placed at the end of leg 2. A distance of ΔLS (the step depth) displaces these mirrors from each other. The maximum difference in length between leg 1 and leg 2 is then given by:

$$\Delta LT = N * \Delta LS,$$

where each mirror adds a distance of ΔLS (the step depth) to the path length difference.

When the interferometer is scanned, the acquired interferogram contains a superposition of all of the input optical frequencies. This is sampled by each mirror element or each position of a scanning mirror. The step size is determined by the lowest wavelength of light that exists in the interferometer. To capture the smallest wavelength without creating aliasing and other undesirable features, the step depth, ΔLS of the mirrors must be less than half the minimum wavelength:

$$\Delta LS = \frac{1}{2} n_{min} \lambda_{min},$$

where $\lambda_{min}$ is the minimum wavelength of light entering the interferometer and $n_{min}$ is the index of refraction at the minimum wavelength.

The number of steps that the multimirror or the electrostatic actuated mirror traverses during a scan determines the spectral resolution of the miniature interferometer. A larger number of steps improves the spectral resolution. The Fourier transform spectrophotometer operates naturally in terms of wavenumber rather than wavelength. In terms of wavenumbers, the wavenumber resolution is given by:

$$k_2 - k_1 = \Delta k = \frac{2\pi}{N * \Delta LS},$$

where Δk is the wavenumber resolution and ΔLS is the step distance, or sampling distance. Converting that to wavelength gives a wavelength resolution, Δλ, that is a function of λ:

$$\lambda_2 - \lambda_1 = \Delta\lambda = \frac{n_2 \lambda_2 * n_1 \lambda_1}{N * \Delta LS} \approx \frac{n^2 \lambda^2}{N * \Delta LS}$$

Table 1 below shows a table of design specifications to achieve a 1750 cm$^{-1}$ wavenumber resolution, or an average 1 nm wavelength resolution within wavelength range of 200 nm-800 nm. Since the optical path difference of the two legs of the interferometer are completely contained within the same medium this a closed form solution, ignoring only error terms such as misalignment and lack of fully collimated light over the bandwidth of operation.

TABLE 1

Multimirror Design Parameters

| Parameter | Value |
| --- | --- |
| N | 900 |
| ΔLS | 155.9 nm |
| ΔLT | 140.3 μm |
| res$_{200\ nm}$ | 0.65 nm |
| res$_{800\ nm}$ | 10.9 nm |

The difficulty in achieving 155 nm control of interferometer distances over a 140 μm scan length has been the difficult challenge both in developing a Fourier transform spectrophotometer for UV operation and in miniaturizing the spectrophotometer. However, the precision and alignment capabilities involved in the microfabrication techniques utilized enables this level of accuracy and control in this invention.

The initial intent of this invention was to analyze chemical concentrations in portable and embedded systems. However, other embodiments or portions of the device can be envisioned that perform different applications. For example, the miniature spectrophotometer can be utilized in other interferometric devices such as in polarimetric analysis, coherence length analyzers, and other systems. In addition, the multi step mirror can be employed as a separate component in other optical systems, such as in adaptive optics devices, multispectral imagers, and beam steerers. The multimirror can also be used in a Fabrey-Perot interferometer, with the multimirror used as an etalon to block certain wavelengths of light.

Furthermore, the fabrication processes for the components, including the multi-mirror and the microoptics bench, can be different. Instead of using multilevel binary processing for the multimirror, other processes including standard etching and lithography, grey-scale lithography, and molding or embossing processes may be used. Instead of silicon micromachining, other fabrication processes such as LIGA, embossing, and molding may be used to realize the mounts and alignment structures for the optical components.

Finally, the basic components of the microspectrophotometer can be altered in form, as long as the function is not altered, without being beyond the scope of this disclosure, For example, the illustrated embodiment uses a ball lens for collimating the light, but a GRIN lens or other type of collimator may be used.

What is claimed is:

1. A miniature Michelson interferometer comprising a cube beamsplitter monolithically integrated with an optical path modulator, the cube beamsplitter comprising a static path side and a differential path side, the optical path modulator comprising:
   a multi-stepped mirror array in physical contact with the differential path side of the cube beamsplitter, comprising a plurality of stepped mirror elements, the stepped mirror elements having a step height, the step height being a function of x-direction step position and y-direction step position on the multi-stepped mirror array; and
   a stationary mirror in physical contact with the static path side of the cube beamsplitter.

2. The miniature Michelson interferometer of claim 1, further comprising a substrate and a collimating lens.

3. The miniature Michelson interferometer of claim 2, further comprising a mounting structure for an optical fiber, the mounting structure comprising:
   a channel, the channel having a first end and a second end;
   an aperture, the aperture defined by an aperture wall, the aperture wall being operatively connected to the second end of the channel and substantially perpendicular to the channel;
   a first wall, wherein the first wall is operably connected to a first side of the aperture wall; and,
   a second wall, wherein the second wall is operably connected to a second side of the aperture wall.

4. The miniature Michelson interferometer of claim 3, wherein the collimating lens is a ball lens and wherein the first wall is disposed such that it forms a first acute interior angle relative to the long axis of the channel, and wherein the second wall is disposed such that it forms a second acute interior angle relative to the long axis of the channel, whereby the optical fiber passively aligns with the collimating lens.

5. The miniature Michelson interferometer of claim 4, wherein the first acute interior angle and the second acute interior angle are approximately 43 degrees.

6. The miniature Michelson interferometer of claim 1, wherein the step height is a function of a series of stepped columns, wherein the step height of a column decreases one increment of step height with each increment of y-direction step position and the step height of a first step of a next column in the x-direction is one increment of step height lower than a last step of a prior column.

7. The miniature Michelson interferometer of claim 1, wherein the step height is a serpentine function of x-direction step position and y-direction step position on the mirror.

8. The miniature Michelson interferometer of claim 1, wherein the step height is a concentric spiral function of x-direction step position and y-direction step position on the mirror.

* * * * *